(12) United States Patent
Endo (10) Patent No.: US 11,950,757 B2
(45) Date of Patent: Apr. 9, 2024

(54) MEDICAL IMAGE PROCESSING APPARATUS

(71) Applicant: FUJIFILM Corporation, Tokyo (JP)

(72) Inventor: Maiko Endo, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 565 days.

(21) Appl. No.: 17/169,530

(22) Filed: Feb. 7, 2021

(65) Prior Publication Data
US 2021/0153821 A1 May 27, 2021

Related U.S. Application Data

(63) Continuation of application No. PCT/JP2019/022046, filed on Jun. 3, 2019.

(30) Foreign Application Priority Data

Aug. 20, 2018 (JP) ................... 2018-153823

(51) Int. Cl.
*A61B 1/00* (2006.01)
*A61B 5/00* (2006.01)
(Continued)

(52) U.S. Cl.
CPC .... *A61B 1/00006* (2013.01); *A61B 1/000094* (2022.02); *A61B 5/743* (2013.01);
(Continued)

(58) Field of Classification Search
CPC .......... A61B 1/00006; A61B 1/000094; A61B 5/743; A61B 5/7485; A61B 1/0005;
(Continued)

(56) References Cited

U.S. PATENT DOCUMENTS 11,100,645 B2 * 8/2021 Kim ....................... G16H 30/20
2008/0039692 A1 * 2/2008 Hirakawa ................ A61B 1/04
600/160

(Continued)

FOREIGN PATENT DOCUMENTS

| CN | 102740757 | 10/2012 |
| EP | 3360461 | 8/2018 |

(Continued)

OTHER PUBLICATIONS

"Search Report of Europe Counterpart Application", dated Jan. 31, 2022, pp. 1-6.

(Continued)

*Primary Examiner* — Michael R Neff
(74) *Attorney, Agent, or Firm* — JCIPRNET (57) ABSTRACT

A bar is displayed in a second region. In an undetected state in which a region of interest is not detected, the length of the bar is 0, and when the undetected state transitions to a detected state in which the region of interest is detected, the bar increases in length over time. In addition, when the detected state transitions to the undetected state, display of the bar is continued with the length fixed. Thus, even in the undetected state, it is known that the region of interest has been previously detected. In addition, even in the undetected state, the region-of-interest detected duration is known from the length of the bar.

18 Claims, 7 Drawing Sheets

(51) Int. Cl.
  *G06T 7/00* (2017.01)
  *G06V 10/25* (2022.01)
  *G06V 10/764* (2022.01)
  *G06V 10/82* (2022.01)
  *A61B 5/055* (2006.01)
  *A61B 6/46* (2024.01)

(52) U.S. Cl.
  CPC .......... *A61B 5/7485* (2013.01); *G06T 7/0012* (2013.01); *G06V 10/25* (2022.01); *G06V 10/764* (2022.01); *G06V 10/82* (2022.01); *A61B 1/0005* (2013.01); *A61B 5/055* (2013.01); *A61B 6/463* (2013.01); *A61B 6/469* (2013.01); *G06T 2207/10068* (2013.01)

(58) Field of Classification Search
  CPC ......... A61B 5/055; A61B 6/463; A61B 6/469; G06V 10/25; G06V 10/82; G06V 10/764; G06T 7/0012; G06T 2207/10068
  USPC ........................................................ 382/128
  See application file for complete search history.

(56) References Cited

U.S. PATENT DOCUMENTS

| | | | |
|---|---|---|---|
| 2008/0303898 A1* | 12/2008 | Nishimura | G16H 40/63 348/E7.085 |
| 2012/0274754 A1 | 11/2012 | Tsuruoka | |
| 2014/0180087 A1 | 6/2014 | Millett et al. | |
| 2018/0249900 A1 | 9/2018 | Imaizumi et al. | |
| 2019/0239718 A1 | 8/2019 | Iwaki | |

FOREIGN PATENT DOCUMENTS

| | | |
|---|---|---|
| JP | 2001120538 | 5/2001 |
| JP | 2009142552 | 7/2009 |
| JP | 2009233177 | 10/2009 |
| JP | 2010035756 | 2/2010 |
| JP | 2011160848 | 8/2011 |
| JP | 2012232144 | 11/2012 |
| JP | 2013135776 | 7/2013 |
| JP | 2016508758 | 3/2016 |
| JP | 2017042219 | 3/2017 |
| WO | 2017081976 | 5/2017 |
| WO | 2018078724 | 5/2018 |

OTHER PUBLICATIONS

"Office Action of Japan Counterpart Application", dated Mar. 15, 2022, with English translation thereof, p. 1-p. 8.
"International Search Report (Form PCT/ISA/210) of PCT/JP2019/022046," dated Aug. 20, 2019, with English translation thereof, pp. 1-5.
"Written Opinion of the International Searching Authority (Form PCT/ISA/237) of PCT/JP2019/022046," dated Aug. 20, 2019, with English translation thereof, pp. 1-16.
"Office Action of China Counterpart Application", dated Sep. 15, 2023, with English translation thereof, pp. 1-14.

* cited by examiner

MEDICAL IMAGE PROCESSING APPARATUS

CROSS-REFERENCE TO RELATED APPLICATIONS

This application is a Continuation of PCT International Application No. PCT/JP2019/022046 filed on 3 Jun. 2019, which claims priority under 35 U.S.C § 119(a) to Japanese Patent Application No. 2018-153823 filed on 20 Aug. 2018. The above application is hereby expressly incorporated by reference, in its entirety, into the present application.

BACKGROUND OF THE INVENTION

1. Field of the Invention

The present invention relates to a medical image processing apparatus using an analysis result of a medical image.

2. Description of the Related Art

In the medical field, by using a medical image such as an endoscopic image, an X-ray image, a computed tomography (CT) image, or a magnetic resonance (MR) image, image diagnosis such as diagnosis of a patient's condition or follow-up is made. On the basis of such image diagnosis, physicians or the like determine a treatment policy or the like.

In recent years, in image diagnosis using a medical image, automatic recognition processing is being performed on a region of interest to be observed with attention to a lesion, a tumor, or the like in an organ by a medical image processing apparatus analyzing a medical image. In particular, through machine learning such as deep learning, information about the region of interest is leant from previous medical images, and the medical image processing apparatus performs recognition processing on a region of interest on the basis of the information acquired through learning, with dramatically high accuracy.

For example, JP2011-160848A (corresponding to US2012/0274754A1) describes an endoscope (medical image processing apparatus) that displays an alert if a region of interest is detected. JP2011-160848A also describes a configuration that continues displaying the alert even if the region of interest becomes out of a screen. This can prevent a problem of failing to notice the region of interest although it is detected.

SUMMARY OF THE INVENTION

However, it is difficult to say that the apparatus described in JP2011-160848A above takes sufficient measures against failing to notice the region of interest. That is, since display of the alert is continued even if the region of interest becomes out of the screen, JP2011-160848A can prevent the region of interest from being missed in this light. However, in a case where, for example, regions of interest are consecutively detected and a region of interest detected later is not noticed although a previously detected region of interest is noticed, even if display of the alert detected later is continued, the alert may be misunderstood as an alert of the previously detected region of interest and may be ignored, failing to notice the region of interest detected later. In particular, if a duration during which the region of interest is detected (duration from entering a detected state in which the region of interest is detected until entering an undetected state in which the region of interest is not detected (region-of-interest detected duration)) is short, the problem of failing to notice it becomes more serious.

The present invention has been made in view of the above background, and an object thereof is to prevent a region of interest from being missed more reliably.

In order to solve the above problem, a medical image processing apparatus according to the present invention includes:

a medical image acquiring unit that acquires a medical image obtained by capturing an image of an observation target;

a region-of-interest detecting unit that detects, from the medical image, a region of interest including a target to be focused in the observation target;

a measurement unit that measures a region-of-interest detected duration that is a duration from entering a detected state in which the region of interest is detected until entering an undetected state in which the region of interest is not detected; and a display control unit that causes a display unit to display the region-of-interest detected duration.

The medical image processing apparatus may further include:

a threshold-value storage unit that stores a threshold value to be used for determining whether the region-of-interest detected duration is long or short, in which it is determined whether the region-of-interest detected duration is less than or equal to the threshold value, and if it is determined that the region-of-interest detected duration is less than or equal to the threshold value, the display control unit may cause the display unit to display the region-of-interest detected duration.

Even if the detected state transitions to the undetected state, if a number of frames or time for the undetected state is less than or equal to a threshold value, the measurement unit may assume that the detected state is continued and measure the region-of-interest detected duration.

The display control unit may cause the display unit to display the region-of-interest detected duration regarding the region of interest detected for the same target to be focused.

The display control unit may cause the display unit to display an elapsed time after entering the detected state in which the region of interest is detected.

The display control unit may cause the display unit to display the elapsed time in a form of a time bar that changes in length in accordance with the elapsed time.

The display control unit may increase the length of the time bar in accordance with the elapsed time.

The display control unit may decrease the length of the time bar in accordance with the elapsed time.

The display control unit may cause the display unit to display the elapsed time by using a numeric value or a character.

The medical image acquiring unit may acquire a plurality of medical images by capturing images of the observation target consecutively in a certain cycle, and the elapsed time may be calculated from a number of the medical images acquired after entering the detected state in which the region of interest is detected.

The display control unit may cause the display unit to display a history of a measurement result of the region-of-interest detected duration.

According to the present invention, since the region-of-interest detected duration is displayed, on the basis of a difference in the displayed region-of-interest detected duration, it is possible to prevent misunderstanding with another region of interest (user's misunderstanding that the displayed region-of-interest detected duration is of a region of interest noticed by the user, although the displayed region-of-interest detected duration is of a region of interest not noticed by the user), preventing the region of interest from being missed more reliably.

BRIEF DESCRIPTION OF THE DRAWINGS

FIG. 1 is a block diagram illustrating a medical image processing apparatus, an endoscope apparatus, and the like;

DESCRIPTION OF THE PREFERRED EMBODIMENTS

Figure 1:
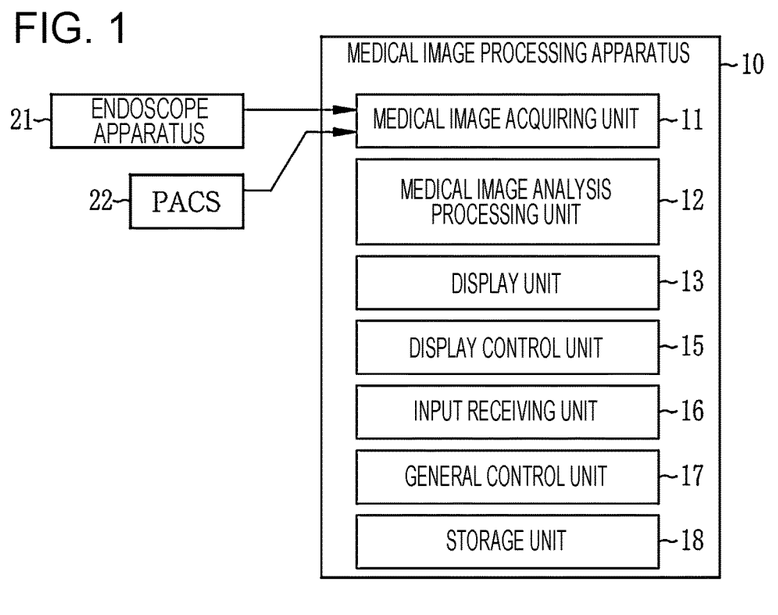

As illustrated in FIG. 1, a medical image processing apparatus 10 includes a medical image acquiring unit 11, a medical image analysis processing unit 12, a display unit 13, a display control unit 15, an input receiving unit 16, a general control unit 17, and a storage unit 18.

The medical image acquiring unit 11 acquires a medical image (image obtained by capturing an image of an observation target such as the inside of a patient's body cavity) directly from an endoscope apparatus 21 or the like or through a management system or another information system, such as a picture archiving and communication system (PACS) 22. The medical image is a still image or a moving image (so-called examination moving image). In a case where the medical image is a moving image, the medical image acquiring unit 11 can acquire frame images constituting the moving image as still images after examination. In addition, in a case where the medical image is a moving image, display of the medical image includes, not only displaying one typical frame still image constituting the moving image, but also reproducing the moving image once or a plurality of times. In addition, the medical image acquired by the medical image acquiring unit 11 includes, not only an image captured by a physician with a medical apparatus such as the endoscope apparatus 21, but also an image automatically captured by a medical apparatus such as the endoscope apparatus 21 regardless of an image pickup instruction from a physician. Note that both the medical image processing apparatus 10 and the endoscope apparatus 21 perform image processing by using a medical image in this embodiment, and thus, each of the medical image processing apparatus 10 and the endoscope apparatus 21 corresponds to a medical image processing apparatus according to the present invention.

In a case where a plurality of medical images may be acquired, the medical image acquiring unit 11 can selectively acquire one or more medical images from these medical images. In addition, the medical image acquiring unit 11 can acquire a plurality of medical images acquired in a plurality of mutually different examinations. For example, either or both of a medical image acquired in a previously performed examination and a medical image acquired in the most recent examination can be acquired. That is, the medical image acquiring unit 11 can acquire a medical image or medical images as appropriate.

In this embodiment, a plurality of medical images including a photographic subject image are acquired. More specifically, in a case of acquiring a plurality of medical images captured in a single specific examination, the plurality of medical images are acquired from a series of medical images. In addition, in this embodiment, the medical image processing apparatus 10 is connected to the endoscope apparatus 21 and acquires the medical images from the endoscope apparatus 21. That is, the medical images in this embodiment are endoscopic images.

The display unit 13 is a display that displays the medical images acquired by the medical image acquiring unit 11 and an analysis result of the medical image analysis processing unit 12. A monitor or a display included in a device or the like to which the medical image processing apparatus 10 is connected may be shared and used as the display unit 13 of the medical image processing apparatus 10. The manner of the display unit 13 displaying the medical images and the analysis result is controlled by the display control unit 15.

The input receiving unit 16 receives inputs from a mouse, a keyboard, or other operation devices connected to the medical image processing apparatus 10. Operations of the units of the medical image processing apparatus 10 can be controlled by using these operation devices.

The general control unit 17 generally controls the operations of the units of the medical image processing apparatus 10. In a case where the input receiving unit 16 receives an operation input using an operation device, in accordance with the operation input, the general control unit 17 controls the units of the medical image processing apparatus 10.

The storage unit 18 stores a still image of the medical image or the like in a storage device (not illustrated) such as a memory included in the medical image processing apparatus 10 or a storage device (not illustrated) included in a medical apparatus such as the endoscope apparatus 21 or the PACS 22.

Figure 2:
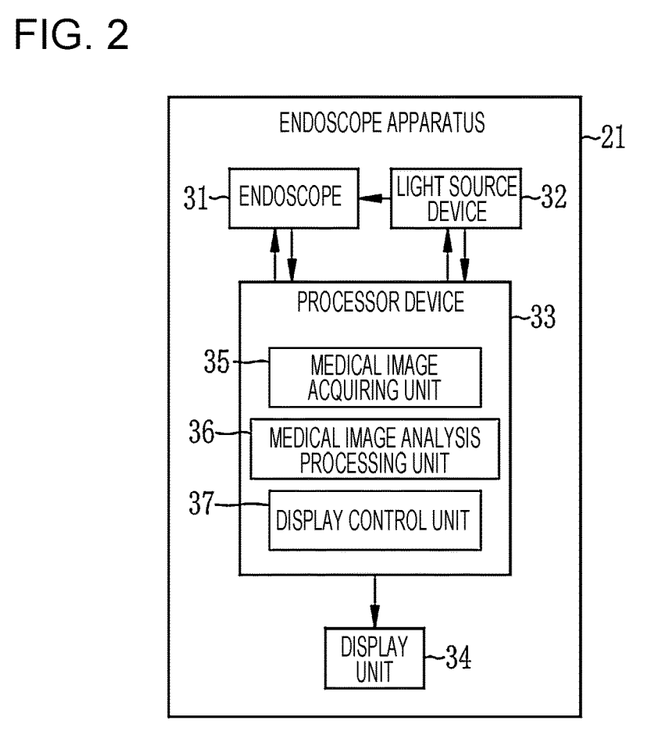
FIG. 2 is a block diagram illustrating the endoscope apparatus.

As illustrated in FIG. 2, the endoscope apparatus 21 to which the medical image processing apparatus 10 is connected in this embodiment has an endoscope 31, a light source device 32, a processor device 33, and a display unit 34. The endoscope 31 acquires an image by capturing an image of a photographic subject irradiated with at least any of light of a white wavelength range or light of a particular wavelength range. The light source device 32 irradiates the inside of the photographic subject with illumination light through the endoscope 31. The display unit 34 displays an endoscopic image captured with the endoscope 31 or the like. The light of the particular wavelength range used by the endoscope 31 as illumination light is, for example, light of a shorter-wavelength range than a green wavelength range, and is, in particular, light of a visible wavelength range of blue or violet.

The processor device 33 includes a medical image acquiring unit 35, a medical image analysis processing unit 36, and a display control unit 37. The medical image acquiring unit 35 acquires a medical image output from the endoscope 31. The medical image analysis processing unit 36 performs analysis processing on the medical image acquired by the medical image acquiring unit 35. Details of processing performed in the medical image analysis processing unit 36 are substantially the same as details of processing performed in the medical image analysis processing unit 12 of the medical image processing apparatus 10. The display control unit 37 causes the display unit 34 to display a medical image obtained by the medical image analysis processing unit 36. The processor device 33 is connected to the medical image processing apparatus 10. Note that the display unit 34 is equivalent to the display unit 13, the medical image acquiring unit 35 is substantially the same as the medical image acquiring unit 11, the medical image analysis processing unit 36 is substantially the same as the medical image analysis processing unit 12, and the display control unit 37 is substantially the same as the display control unit 15.

Figure 3:
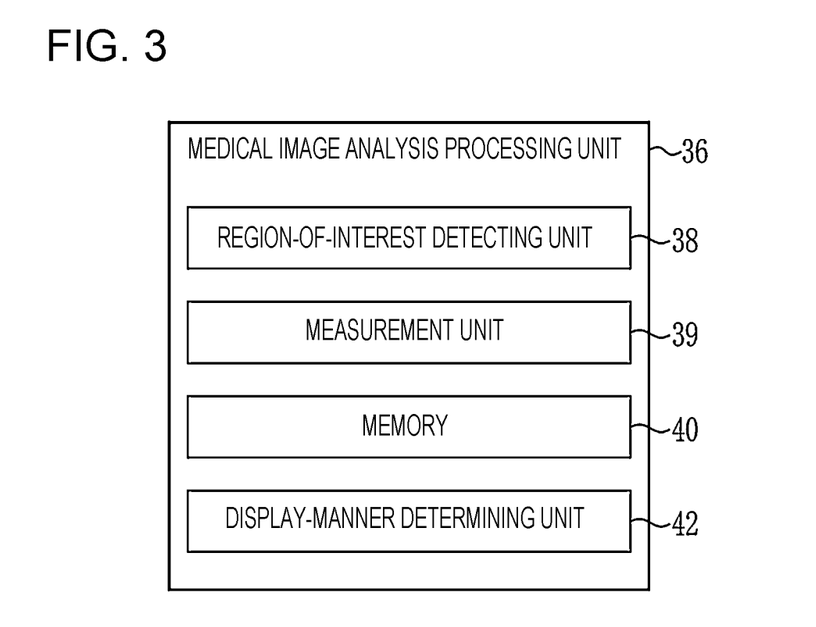
FIG. 3 is a block diagram illustrating functions of a medical image analysis processing unit.

The medical image analysis processing unit 36 performs analysis processing by using the medical image acquired by the medical image acquiring unit 35. As illustrated in FIG. 3, the medical image analysis processing unit 36 includes a region-of-interest detecting unit 38, a measurement unit 39, a memory 40, and a display-manner determining unit 42. The region-of-interest detecting unit 38 performs region-of-interest detection processing for detecting a region of interest (region including a target to be focused in the observation target) from the medical image. As the region-of-interest detection processing, for example, a neural network (NN), a convolutional neural network (CNN), AdaBoost, a random forest, or the like may be employed. In addition, as the region-of-interest detection processing, the region of interest 47 may be detected on the basis of a feature quantity obtained as color information of a medical image, a gradient of a pixel value, or the like. Note that the gradient of the pixel value or the like changes depending on, for example, the shape of the photographic subject (e.g., global ups and downs or local depression or projection in a mucous membrane), color (color of, for example, inflammation, bleeding, redness, or whitening due to atrophy), feature of an organ (e.g., blood vessel thickness, depth, density, or a combination thereof), feature of a structure (e.g., pit pattern), or the like.

Note that the region of interest 47 detected by the region-of-interest detecting unit 38 is a region including, for example, a lesion part typified by a cancer, a benign tumor part, an inflammation part (including, not only a so-called inflammation, but also a part with a change such as bleeding or atrophy), a marking part marked by cauterization by heating or colored with a colorant, a fluorescent agent, or the like, and a biopsy performing part where a biopsy is performed. That is, the region of interest 47 may be a region including a lesion, a region that may possibly be a lesion, a region subjected to certain treatment including a biopsy, a treatment tool including a clip or forceps, a region that needs close observation, regardless of the possibility of a lesion, such as a dark region (a region behind a fold or depth of a luminal organ where observation light is difficult to be delivered), or the like. In the endoscope apparatus 21, the region-of-interest detecting unit 38 detects, as the region of interest 47, a region including at least any of the lesion part, the benign tumor part, the inflammation part, the marking part, or the biopsy performing part.

The measurement unit 39 measures an elapsed time after entering the detected state in which the region of interest is detected and a region-of-interest detected duration, which is a duration from entering the detected state in which the region of interest is detected until entering an undetected state in which the region of interest is not detected. In this embodiment, the measurement unit 39 performs measuring (measures time) by using a built-in clock (not illustrated) built in a medical apparatus such as the medical image processing apparatus 10 or the endoscope apparatus 21 or the PACS 22. Note that in a case where the medical image is, for example, a moving image constituted by a plurality of images obtained by capturing images consecutively in a certain cycle, from the number of images obtained after entering the detected state, the elapsed time after entering the detected state can be calculated. Similarly, from the number of images obtained after entering the detected state until entering the undetected state, the region-of-interest detected duration can be calculated. In this manner, the time may be measured on the basis of the number of images obtained during a duration that is a time-measurement target.

Upon measurement (time measurement) of the elapsed time after entering the detected state and the region-of-interest detected duration, information obtained through measurement is stored in the memory 40. The memory 40 also stores a threshold value for determining whether the region-of-interest detected duration is long or short. That is, the memory 40 functions as a threshold-value storage unit according to the present invention.

Note that the region-of-interest detected duration is measured for each region of interest detected for the same target to be focused, and each time the measurement is performed, the memory 40 sequentially stores the region-of-interest detected duration for each region of interest detected for the same target to be focused. In this embodiment, it is assumed that only a single target to be focused is present in a single medical image and that the duration until entering the undetected state from the detected state is simply the region-of-interest detected duration regarding the region of interest detected for the same target to be focused. However, it may be determined whether the detected region of interest is a region of interest detected for the same target to be focused by using a feature of the region of interest, such as the location, shape, size, and/or color thereof, and the region-of-interest detected duration may be the duration from when the region of interest detected for the same target to be focused enters the detected state until when it enters the undetected state.

Furthermore, although the region of interest for the same target to be focused is being detected, for example, a defective image mixed in a captured image may cause the undetected state only for a short duration (e.g., 2 frames). Thus, if the duration of the undetected state is a short duration, specifically, less than or equal to a threshold value (e.g., within 10 frames or within 0.1 seconds), it may be assumed that the region of interest for the same target to be focused is detected with the undetected state intervened. In addition, even if the detected state transitions to the undetected state as described above, if the undetected state is for a short duration, specifically, less than or equal to the threshold value, the region-of-interest detected duration may be measured by assuming that the detected state is continued.

The display-manner determining unit 42 determines display manners of the medical image, the region-of-interest detected duration, and the elapsed time after the region of interest has been detected. In accordance with the determined display manners, the display control unit 37 causes the display unit 34 to display the medical image, the region-of-interest detected duration, and the elapsed time.

Figure 4:
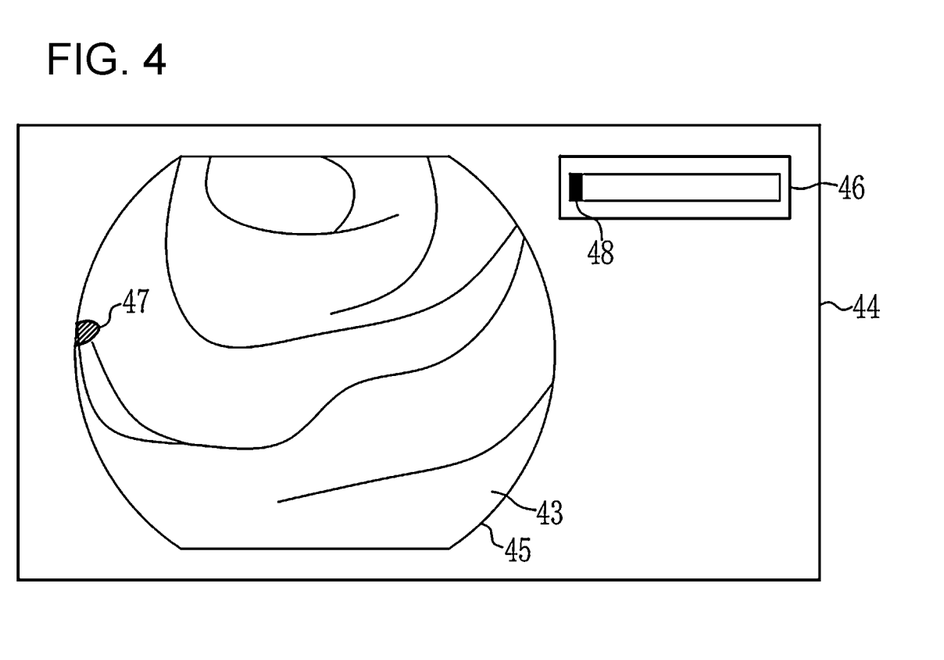
FIG. 4 is an explanatory diagram illustrating a display manner of an elapsed time after entering a detected state.
Figure 5:
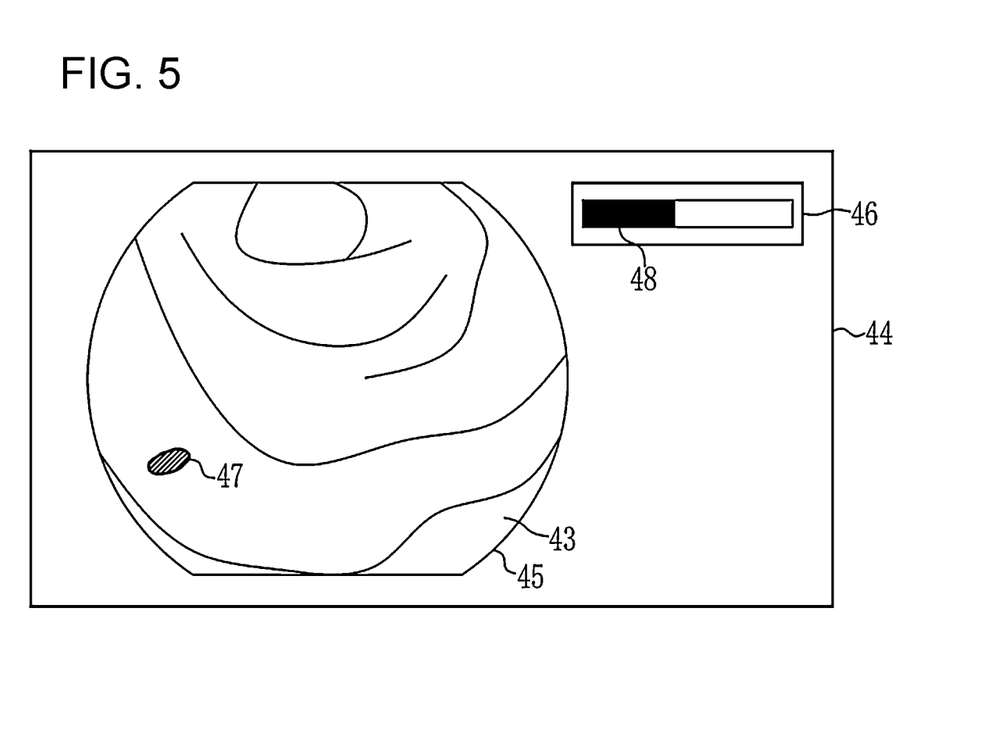
FIG. 5 is an explanatory diagram illustrating a display manner of an elapsed time after entering a detected state.
Figure 6:
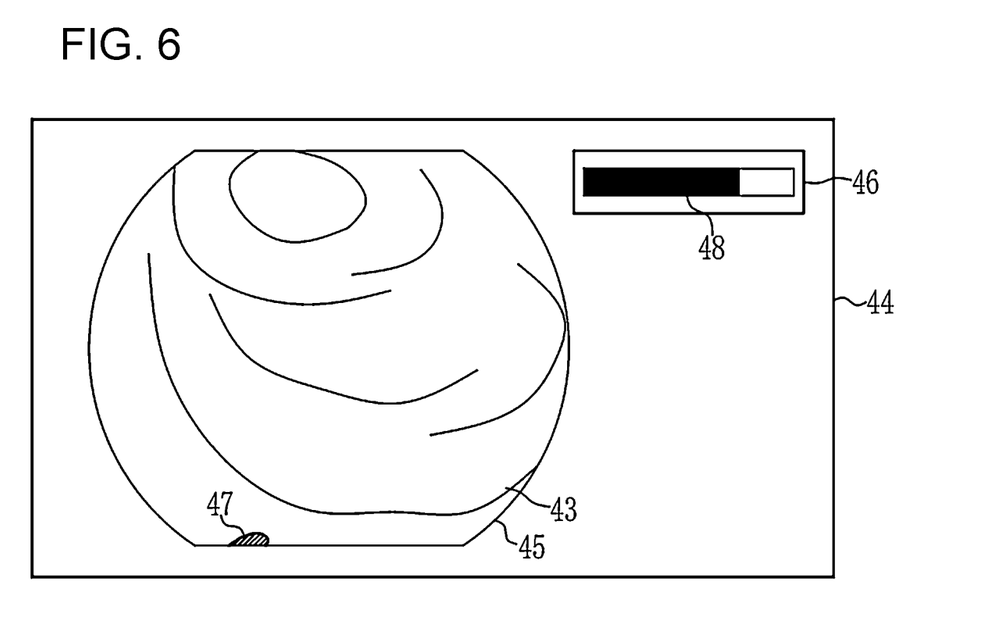
FIG. 6 is an explanatory diagram illustrating a display manner of an elapsed time after entering a detected state.
Figure 7:
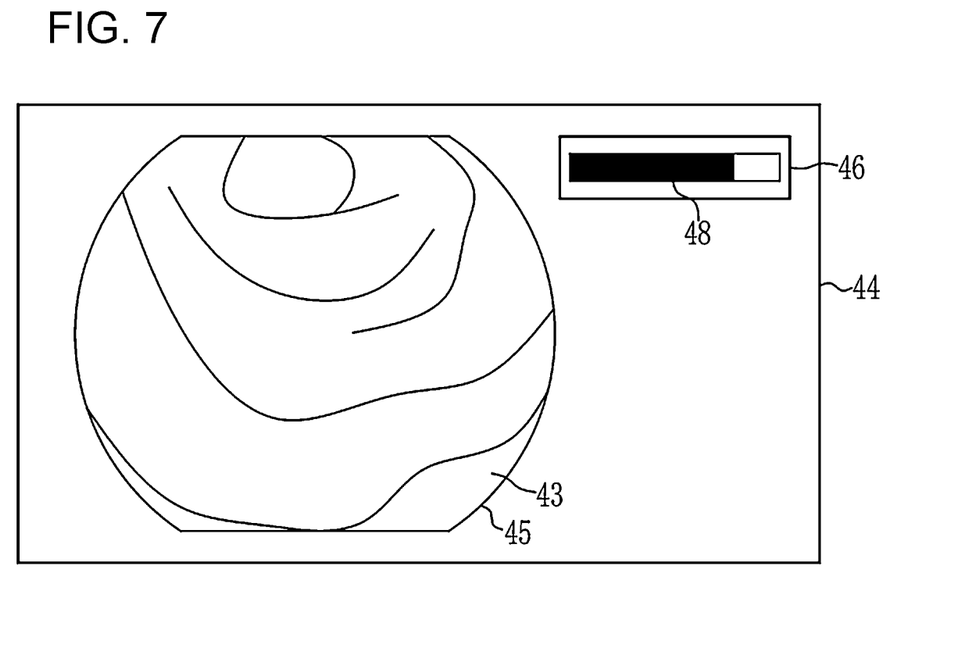
FIG. 7 is an explanatory diagram illustrating a display manner of a region-of-interest detected duration.

As illustrated in FIG. 4 to FIG. 7, in this embodiment, for example, on a display screen 44 (hereinafter also simply referred to as screen) displayed on the display unit 34, a first region 45 for displaying the medical image 43 and a second region 46 for displaying the region-of-interest detected duration and the elapsed time are provided, and the display-manner determining unit 42 determines the display manners of images to be displayed in these first and second regions 45 and 46. Note that FIG. 4 to FIG. 7 illustrate display screens 44 displaying, in screens (in the first region 45), a series of medical images 43 that are sequentially acquired in the order from FIG. 4 to FIG. 7, along with an endoscope examination. Each of FIG. 4, FIG. 5, and FIG. 6 illustrates a detected state in which a region of interest 47 is detected, whereas FIG. 7 illustrates an undetected state in which the region of interest 47 is not detected.

In the first region 45 in the detected state, the region of interest 47 (in the detected state) is reported by being displayed with the region of interest 47 being hatched (see FIG. 4, FIG. 5, and FIG. 6). In addition, in the first region 45 in the undetected state, only the medical image 43 is displayed (see FIG. 7).

Note that the region of interest 47 is reported by being hatched in this embodiment. However, the present invention is not limited to this. The region of interest 47 may also be reported by being colored. Alternatively, the region of interest 47 may also be reported by the outline thereof being colored or emphasized. Further alternatively, the region of interest 47 may also be reported by being displayed in a blinking manner or by the outline thereof being displayed in a blinking manner, for example. Alternatively, the region of interest 47 may also be reported by being surrounded by a frame or the like. Besides, without limitation to an embodiment of a visual report, audio report may be possible by outputting a notification sound or the like. In this manner, the manner for reporting the region of interest 47 can be freely set.

In the second region 46 in the detected state, the elapsed time after the region of interest 47 has been detected is displayed (see FIG. 4, FIG. 5, and FIG. 6). In this embodiment, the elapsed time is displayed in the form of a bar 48 (time bar). In the initial state (in the undetected state), the length of the bar 48 is 0 (the bar 48 does not appear), and when the undetected state transitions to the detected state, the bar 48 increases in length over time. Thus, the elapsed time after transition to the detected state is known by checking the length of the bar 48. Note that in a case where the elapsed time becomes so long that the length of the bar 48 does not fall within the second region 46, the second region 46 may be enlarged. Alternatively, the bar 48 may be displayed in two stages. Furthermore, as the elapsed time becomes longer, an increase amount of the bar 48 per unit time may be decreased.

In addition, when the detected state transitions to the undetected state, display of the bar 48 displayed in the second region 46 is continued with the length fixed (see FIG. 7). Thus, even in the undetected state in which the region of interest 47 is not currently detected, it is known that the region of interest 47 has been previously detected. In addition, since the length of the bar 48 corresponds to the duration during which the region of interest 47 is detected (the region-of-interest detected duration), even in the undetected state, the region-of-interest detected duration is known from the length of the bar 48. Display of the bar 48 is continued until a new region of interest 47 is detected to enter the detected state, and when the undetected state transitions to the detected state, the bar 48 returns to a state in which the length increases from 0 in accordance with the elapsed time (see FIG. 4, FIG. 5, and FIG. 6).

Note that the above embodiment has described an example in which, regardless of the elapsed time after entering the detected state, the region-of-interest detected duration is displayed (display is continued with the length of the bar 48 fixed) if entering the undetected state. However, the present invention is not limited to this. Although the region of interest 47 with a short elapsed time after entering the detected state is likely to be missed, the region of interest 47 with a long elapsed time after entering the detected state is unlikely to be missed. Thus, the configuration may also be as follows. Only in a case where the elapsed time after entering the detected state is less than or equal to the threshold value stored in the memory 40, the region-of-interest detected duration is displayed, and, in a case where the elapsed time after entering the detected state exceeds the threshold value, the region-of-interest detected duration is not displayed.

In addition, the above embodiment has described an example of a configuration in which, as the elapsed time after entering the detected state becomes longer, the length of the bar 48 increases, that is, the region-of-interest detected duration is longer as the bar 48 is longer. However, the present invention is not limited to this. The bar 48 may be the longest when entering the detected state, and as the elapsed time after entering the detected state becomes longer, the bar 48 may become shorter, and after entering the undetected state, display of the bar 48 may be maintained with the length of the bar 48 fixed. That is, the configuration may also be as follows. It is indicated that the region-of-interest detected duration is longer as the bar 48 is shorter.

Figure 8:
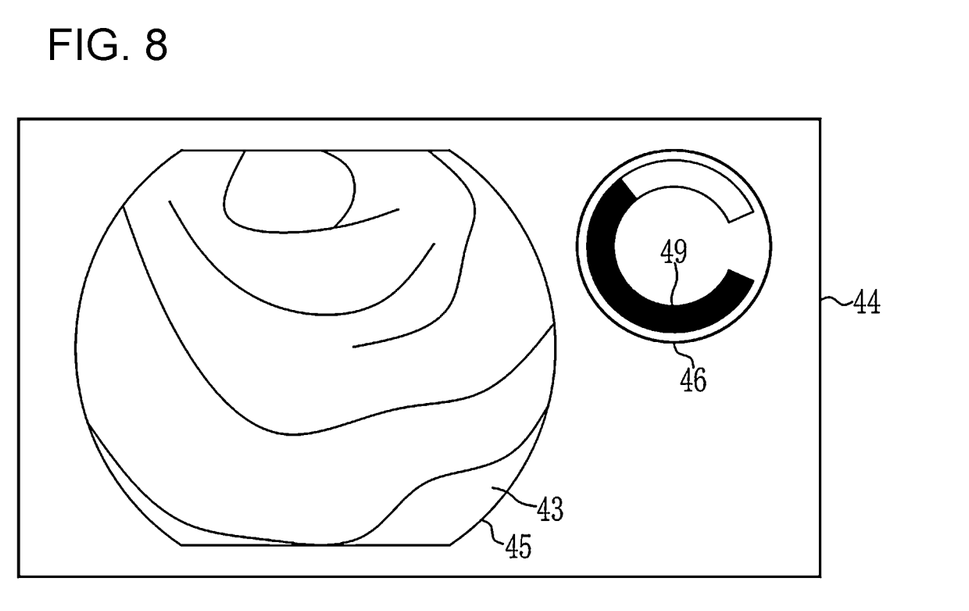
FIG. 8 is an explanatory diagram illustrating a display manner of a region-of-interest detected duration.

In addition, although the above embodiment has described an example of indicating the region-of-interest detected duration by using the linear bar 48, the region-of-interest detected duration may alternatively be indicated by using a circular bar 49 as illustrated in FIG. 8. Note that, in the description with reference to FIG. 8 and subsequent drawings, substantially the same members as those in the above-described embodiment are denoted by substantially the same numerals, and description thereof is omitted.

Figure 9:
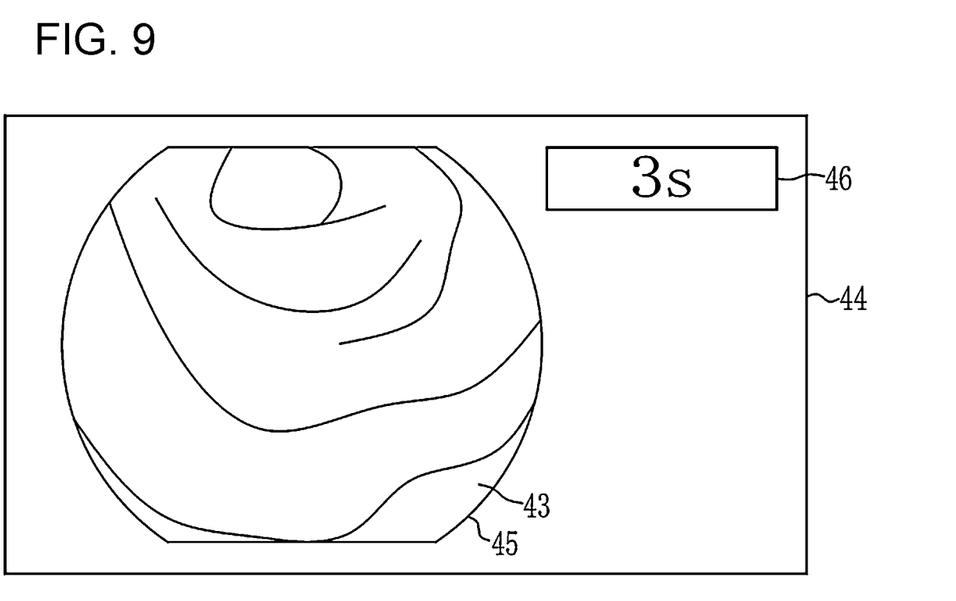
FIG. 9 is an explanatory diagram illustrating a display manner of a region-of-interest detected duration.
Figure 10:
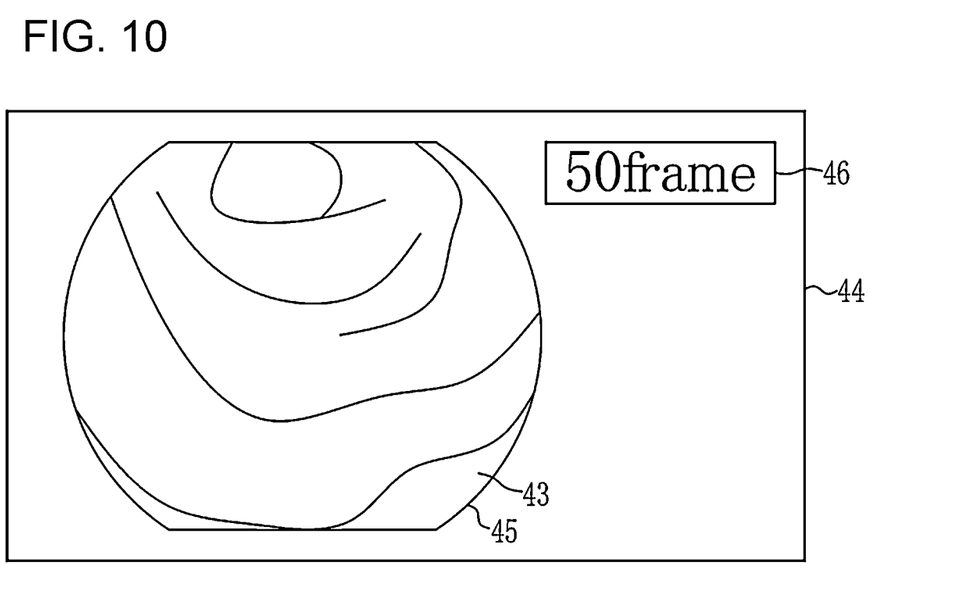
FIG. 10 is an explanatory diagram illustrating a display manner of a region-of-interest detected duration.

In addition, the region-of-interest detected duration may alternatively be indicated by using a numeric value as illustrated in FIG. 9. FIG. 9 illustrates that the current state is the undetected state, but a region of interest that has previously been in the detected state for 3 seconds is present. As a matter of course, the region-of-interest detected duration may also be indicated by using a character. Furthermore, the region-of-interest detected duration may alternatively be indicated by using the number of images as illustrated in FIG. 10. FIG. 10 illustrates the presence of a region of interest that has previously been in the detected state for 50 frames, that is, for the duration during which 50 images (50 frames) are captured.

Figure 11:
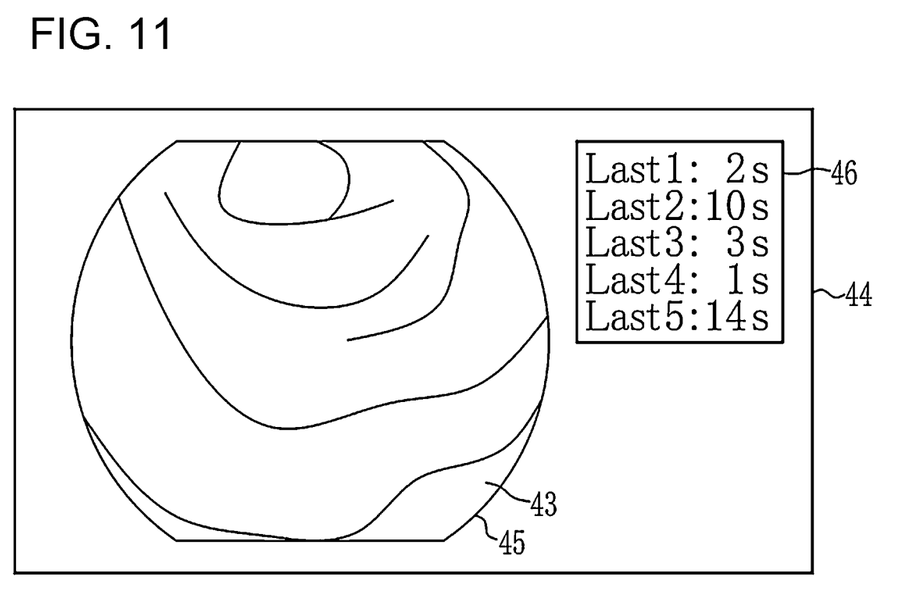
FIG. 11 is an explanatory diagram illustrating a display manner of a region-of-interest detected duration.

In addition, the above embodiment has described an example of a configuration of displaying a most recent region-of-interest detected duration from among measured region-of-interest detected durations. However, as illustrated in FIG. 11, the configuration also may be such that a history of measurement results of the region-of-interest detected durations is displayed. Specifically, the plurality of region-of-interest detected durations may be arranged and displayed in the order of measurement. FIG. 11 illustrates the presence of five regions of interest that have been in the detected state for 2 seconds, 10 seconds, 3 seconds, 1 second, and 14 seconds, in descending order from the most recent one.

In addition, the above embodiment has described an example of a configuration of displaying, in the detected state, the elapsed time after entering the detected state by, for example, increasing the length of the bar over time, and displaying the region-of-interest detected duration after entering the undetected state (display of the bar is maintained with the length of the bar fixed). However, the present invention is not limited to this. The configuration may also be as follows. In the detected state, the elapsed time (the region-of-interest detected duration) is only measured without being displayed, and after entering the undetected state, the region-of-interest detected duration is displayed.

Figure 12:
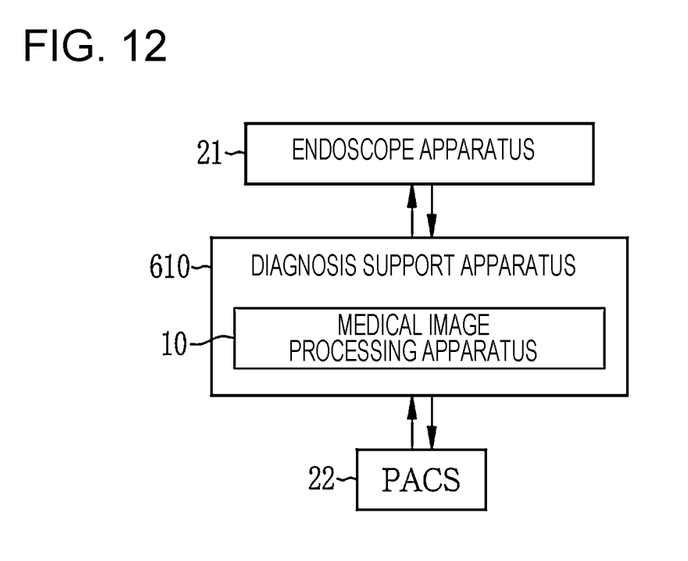
FIG. 12 is a diagnosis support apparatus including the medical image processing apparatus.
Figure 13:
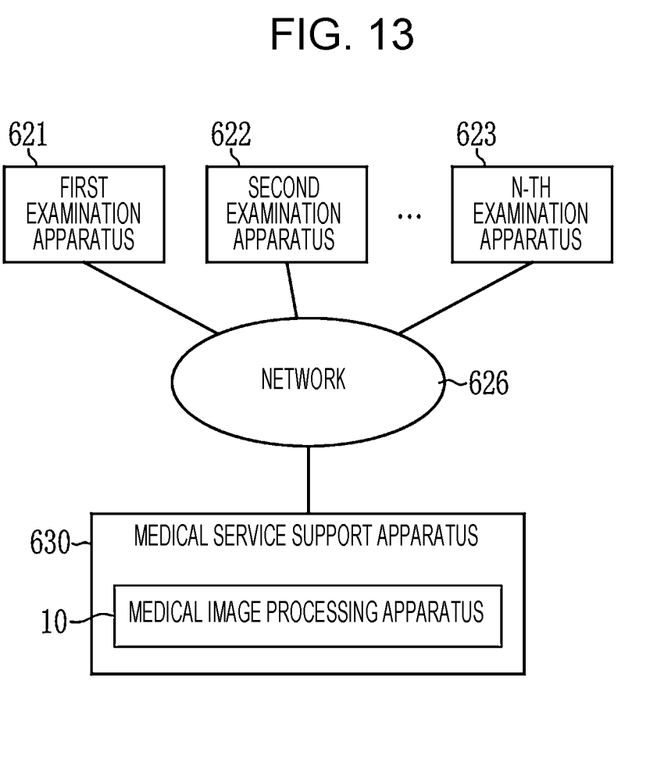
FIG. 13 is a medical service support apparatus including the medical image processing apparatus.

Note that as illustrated in FIG. 12, the medical image processing apparatus 10 according to the above embodiment or other modifications may be included in a diagnosis support apparatus 610 using the endoscope apparatus 21 or other modalities and the PACS 22 in combination. In addition, as illustrated in FIG. 13, the medical image processing apparatus 10 according to the above embodiment or other modifications may be included in a medical service support apparatus 630 that establishes connection with various examination apparatuses via any network 626. The various examination apparatuses are, for example, a first examination apparatus 621, a second examination apparatus 622, . . . , an N-th examination apparatus 623, and the like, each including the endoscope apparatus 21.

Besides, the medical image processing apparatus 10, the endoscope apparatus 21, and various apparatuses or systems including the medical image processing apparatus 10 can be used by making the following various changes, for example.

As the medical image, an ordinary-light image may be used. The ordinary-light image is obtained by radiating light of a white range or light of a plurality of wavelength ranges as the light of the white range.

In a case where an image obtained by radiating the light of the particular wavelength range is used as the medical image, as the particular wavelength range, a range narrower than the white wavelength range may be used.

The particular wavelength range is, for example, a visible wavelength range of blue or green.

In a case where the particular wavelength range is the visible wavelength range of blue or green, the particular wavelength range preferably includes a wavelength range that is greater than or equal to 390 nm and is less than or equal to 450 nm, or is greater than or equal to 530 nm and is less than or equal to 550 nm, and the light of the particular wavelength range preferably has a peak wavelength in the wavelength range that is greater than or equal to 390 nm and is less than or equal to 450 nm, or is greater than or equal to 530 nm and is less than or equal to 550 nm.

The particular wavelength range is, for example, a visible wavelength range of red.

In a case where the particular wavelength range is the visible wavelength range of red, the particular wavelength range preferably includes a wavelength range that is greater than or equal to 585 nm and is less than or equal to 615 nm, or is greater than or equal to 610 nm and is less than or equal to 730 nm, and the light of the particular wavelength range preferably has a peak wavelength in the wavelength range that is greater than or equal to 585 nm and is less than or equal to 615 nm, or is greater than or equal to 610 nm and is less than or equal to 730 nm.

The particular wavelength range may include, for example, a wavelength range in which a light absorption coefficient differs between oxyhemoglobin and deoxyhemoglobin, and the light of the particular wavelength range may have a peak wavelength in the wavelength range in which the light absorption coefficient differs between oxyhemoglobin and deoxyhemoglobin.

In a case where the particular wavelength range includes the wavelength range in which the light absorption coefficient differs between oxyhemoglobin and deoxyhemoglobin, and the light of the particular wavelength range has the peak wavelength in the wavelength range in which the light absorption coefficient differs between oxyhemoglobin and deoxyhemoglobin, the particular wavelength range preferably includes a wavelength range of 400±10 nm, 440±10 nm, or 470±10 nm, or a wavelength range that is greater than or equal to 600 nm and is less than or equal to 750 nm, and the light of the particular wavelength range preferably has a peak wavelength in the wavelength range of 400±10 nm, 440±10 nm, or 470±10 nm, or in the wavelength range that is greater than or equal to 600 nm and is less than or equal to 750 nm.

In a case where the medical image is an inside body image of an inside of a body, the inside body image may have information of fluorescent light emitted by a fluorescence substance in the body.

In addition, as the fluorescent light, fluorescent light obtained by irradiating the inside of the body with excitation light having a peak wavelength that is greater than or equal to 390 nm and is less than or equal to 470 nm may be used.

In a case where the medical image is an inside body image of an inside of a body, as the above-described particular wavelength range, a wavelength range of infrared light may be used.

In a case where the medical image is an inside body image of an inside of a body and the wavelength range of infrared light is used as the above-described particular wavelength range, the particular wavelength range preferably includes a wavelength range that is greater than or equal to 790 nm and is less than or equal to 820 nm, or is greater than or equal to 905 nm and is less than or equal to 970 nm, and the light of the particular wavelength range preferably has a peak wavelength in the wavelength range that is greater than or equal to 790 nm and is less than or equal to 820 nm, or is greater than or equal to 905 nm and is less than or equal to 970 nm.

The medical image acquiring unit 11 may include a special-light-image acquiring unit that acquires a special-light image having a signal in a particular wavelength range on the basis of the ordinary-light image obtained by radiating the light of the white range or by radiating light of a plurality of wavelength ranges as the light of the white range. In this case, the special-light image may be used as the medical image.

The signal in the particular wavelength range may be obtained through a calculation based on color information of RGB or CMY included in the ordinary-light image.

A feature-quantity-image generation unit may be included. The feature-quantity-image generation unit generates a feature-quantity image through a calculation based on at least one of the ordinary-light image that is obtained by radiating the light of the white range or light of a plurality of wavelength ranges as the light of the white range or the special-light image obtained by radiating the light of the particular wavelength range. In this case, the feature-quantity image may be used as the medical image.

Regarding the endoscope apparatus 21, a capsule endoscope may be used as the endoscope 31. In this case, the light source device 32 and part of the processor device 33 may be installed on the capsule endoscope.

In the above embodiment and modifications, a hardware structure of processing units that perform various kinds of processing, such as the medical image acquiring unit 11, the medical image analysis processing unit 12, each unit constituting the medical image analysis processing unit 12, the display control unit 15, the input receiving unit 16, the general control unit 17, the medical image acquiring unit 35, the medical image analysis processing unit 36, the display control unit 37, the region-of-interest detecting unit 38, and the display-manner determining unit 42 is any of the following various processors. Various processors include a central processing unit (CPU) and a graphical processing unit (GPU) that are general-purpose processors functioning as various processing units by executing software (programs), a programmable logic device (PLD) that is a processor in which the circuit configuration is changeable after manufacture, such as field programmable gate array (FPGA), a dedicated electric circuit that is a processor having a circuit configuration that is specially designed to execute various kinds of processing, and the like.

One processing unit may be constituted by one of these various processors, or may be constituted by two or more processors of the same type or different types in combination (e.g., a combination of a plurality of FPGAs, a combination of a CPU and an FPGA, or a combination of a CPU and a GPU). In addition, a plurality of processing units may be constituted by one processor. As a first example for constituting a plurality of processing units with one processor, one processor may be constituted by a combination of one or more CPUs and software, and this processor may function as a plurality of processing units, as typified by a computer such as a client or a server. As a second example, a processor may be used that implements the functions of the entire system including a plurality of processing units with one integrated circuit (IC) chip, as typified by a system on chip (SoC) or the like. In this manner, various processing units are constituted by one or more of the above various processors in terms of hardware structure.

More specifically, the hardware structure of these various processors is electric circuitry constituted by combining circuit elements such as semiconductor elements.

REFERENCE SIGNS LIST 10 medical image processing apparatus
11 medical image acquiring unit
12 medical image analysis processing unit
13 display unit
15 display control unit
16 input receiving unit
17 general control unit
18 storage unit
21 endoscope apparatus
22 picture archiving and communication system (PACS)
31 endoscope
32 light source device
33 processor device
34 display unit
35 medical image acquiring unit
36 medical image analysis processing unit
37 display control unit
38 region-of-interest detecting unit
39 measurement unit
40 memory
42 display-manner determining unit
43 medical image
44 display screen
45 first region
46 second region
47 region of interest
48 bar
49 bar
610 diagnosis support apparatus
621 first examination apparatus
622 second examination apparatus
623 N-th examination apparatus
626 network
630 medical service support apparatus

What is claimed is:

1. A medical image processing apparatus comprising:
a processor configured to:
acquire a medical image obtained by capturing an image of an observation target;
detect, from the medical image, a region of interest including a target to be focused in the observation target;
measure a region-of-interest detected duration that is a duration from entering a detected state in which the region of interest is detected until entering an undetected state in which the region of interest is not detected;
cause a display to display the region-of-interest detected duration, and
a memory that stores a threshold value to be used for determining whether the region-of-interest detected duration is long or short, and
wherein it is determined whether the region-of-interest detected duration is less than or equal to the threshold value, and if it is determined that the region-of-interest detected duration is less than or equal to the threshold value, the processor is configured to cause the display to display the region-of-interest detected duration.

2. The medical image processing apparatus according to claim 1,
wherein the processor is configured to cause the display to display the region-of-interest detected duration regarding the region of interest detected for the same target to be focused.

3. The medical image processing apparatus according to claim 1,
wherein the processor is configured to cause the display to display an elapsed time after entering the detected state in which the region of interest is detected.

4. The medical image processing apparatus according to claim 3,
wherein the processor is configured to cause the display to display the elapsed time in a form of a time bar that changes in length in accordance with the elapsed time.

5. The medical image processing apparatus according to claim 4,
wherein the display control unit increases processor is configured to increase the length of the time bar in accordance with the elapsed time.

6. The medical image processing apparatus according to claim 4,
wherein the processor is configured to decrease the length of the time bar in accordance with the elapsed time.

7. The medical image processing apparatus according to claim 3, wherein the processor is configured to cause the display to display the elapsed time by using a numeric value or a character.

8. The medical image processing apparatus according to claim 3,
wherein the processor is configured to acquire a plurality of medical images by capturing images of the observation target consecutively in a certain cycle, and
wherein the elapsed time is calculated from a number of the medical images acquired after entering the detected state in which the region of interest is detected.

9. The medical image processing apparatus according to claim 1,
wherein the processor is configured to cause the display to display a history of a measurement result of the region-of-interest detected duration.

10. A medical image processing apparatus comprising:
a processor configured to:
acquire a medical image obtained by capturing an image of an observation target,
detect, from the medical image, a region of interest including a target to be focused in the observation target,
measure a region-of-interest detected duration that is a duration from entering a detected state in which the region of interest is detected until entering an undetected state in which the region of interest is not detected; and
cause a display to display the region-of-interest detected duration,
wherein, even if the detected state transitions to the undetected state, if a number of frames or a time after entering the undetected state is less than or equal to a threshold value, the processor is configured to assume that the detected state is continued and measures the region-of-interest detected duration.

11. The medical image processing apparatus according to claim 10,
wherein the processor is configured to cause the display to display the region-of-interest detected duration regarding the region of interest detected for the same target to be focused.

12. The medical image processing apparatus according to claim 10,
wherein the processor is configured to cause the display to display an elapsed time after entering the detected state in which the region of interest is detected.

13. The medical image processing apparatus according to claim 12,
wherein the processor is configured to cause the display to display the elapsed time in a form of a time bar that changes in length in accordance with the elapsed time.

14. The medical image processing apparatus according to claim 13,
wherein the processor is configured to increase the length of the time bar in accordance with the elapsed time.

15. The medical image processing apparatus according to claim 13,
wherein the processor is configured to decrease the length of the time bar in accordance with the elapsed time.

16. The medical image processing apparatus according to claim 12,
wherein the processor is configured to cause the display to display the elapsed time by using a numeric value or a character.

17. The medical image processing apparatus according to claim 12,
wherein the processor configured to acquire a plurality of medical images by capturing images of the observation target consecutively in a certain cycle, and
wherein the elapsed time is calculated from a number of the medical images acquired after entering the detected state in which the region of interest is detected.

18. The medical image processing apparatus according to claim 10,
wherein the processor is configured to cause the display to display a history of a measurement result of the region-of-interest detected duration.

* * * * *